United States Patent [19]

Heveling

[11] Patent Number: 5,310,952

[45] Date of Patent: May 10, 1994

[54] METHOD FOR THE PREPARATION OF 6-HYDROXY-2,5,7,8-TETRAALKYL-2-(4-AMINOPHENOXYMETHYL) CHROMANS

[75] Inventor: Josef Heveling, Naters, Switzerland

[73] Assignees: Lonza Ltd., Gampel/Valais, Switzerland; Sankyo Company Ltd., Tokyo, Japan

[21] Appl. No.: 19,695

[22] Filed: Feb. 19, 1993

[30] Foreign Application Priority Data

Feb. 21, 1992 [CH] Switzerland ............... 532/92

[51] Int. Cl.$^5$ ........................... C07D 311/58
[52] U.S. Cl. ...................... 549/407; 549/401
[58] Field of Search ................. 549/407, 401

[56] References Cited

U.S. PATENT DOCUMENTS 5,030,601 7/1991 Michel et al. ............. 501/103

FOREIGN PATENT DOCUMENTS 0139421 6/1985 European Pat. Off. .
0207581 1/1987 European Pat. Off. .

OTHER PUBLICATIONS

J. Med. Chem., 32, (1989), pp. 421 to 428.
Shibagaki et al., Bull. Chem., Soc., Japan, 61, (1988), pp. 3283 to 3288.

*Primary Examiner*—Nicky Chan
*Attorney, Agent, or Firm*—Fisher, Christen & Sabol

[57] ABSTRACT

A novel process for the preparation of aminochromans of the general formula:

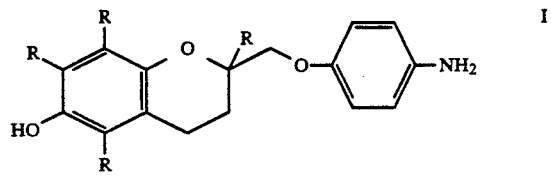

wherein R is a $C_1$–$C_4$ alkyl group. In the process, a nitrochromanone of the general formula:

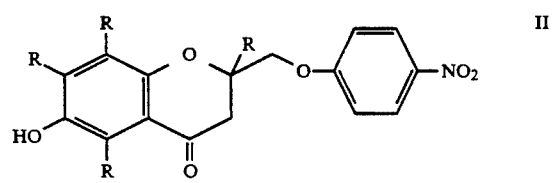

is hydrogenated with hydrogen in the presence of a hydrogenation catalyst. The resultant aminochromanone (III) is reduced using zirconium oxide/isopropanol to the aminochromene (IV). The latter is finally hydrogenated with hydrogen in the presence of a hydrogenation catalyst to give the final product. The aminochromans are useful intermediates for the preparation of hypolipidaemic pharmaceuticals.

20 Claims, No Drawings

METHOD FOR THE PREPARATION OF 6-HYDROXY-2,5,7,8-TETRAALKYL-2-(4-AMINO-PHENOXYMETHYL) CHROMANS

BACKGROUND OF THE INVENTION

1. Field Of The Invention

The invention relates to a novel process for the preparation of 6-hydroxy-2,5,7,8-tetraalkyl-2-(4-aminophenoxymethyl)chromans (aminochroman) of the general formula:

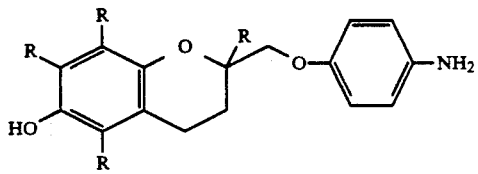

I wherein R denotes a lower alkyl group having 1 to 4 carbon atoms.

2. Background Art

It is known from European Published Patent Application No. 207,581 to prepare aminochromans of the general formula I by first converting a tetraalkyl-2-(4-nitrophenoxymethyl) chroman-4-one into the corresponding chroman-4-ol using sodium borohydride, in a further step dehydrating the chroman-4-ol to the chroman-3-ene in the presence of p-toluenesulphonic acid and in the last step hydrogenating both the nitro group and the chromene double bond using a hydrogenation catalyst to give the final product. This reaction has the disadvantage that a considerable need for working up arises between the individual reaction steps, which impedes conversion of the synthesis to the industrial scale. Additionally, reduction using sodium borohydride is expensive in comparison with catalytic reductions and is problematic from an ecological point of view as the resulting effluents are polluted with boron.

BROAD DESCRIPTION OF THE INVENTION

The main objective of the invention is to provide a synthesis which is simpler than the above described prior art process and which does not have the stated disadvantages thereof. The main objective according to the invention is achieved by the process according to the invention.

Other objectives and advantages of the invention are set out herein or are obvious herefrom to one skilled in the art.

The objectives and advantages of the invention are achieved by the process of the invention.

The invention involves a process for the preparation of 6-hydroxy-2,5,7,8-tetraalkyl-2-(4-aminophenoxymethyl)chromans of the general formula:

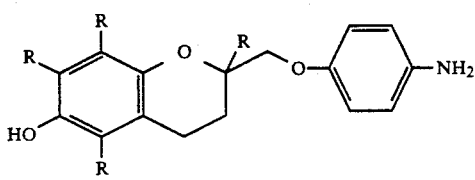

I wherein R is a $C_1$-$C_4$-alkyl group. The process involves, in a first step, hydrogenating a 6-hydroxy-2,5,7,8-tetraalkyl-2-(4-aminophenoxymethyl)chroman-4-one of the general formula:

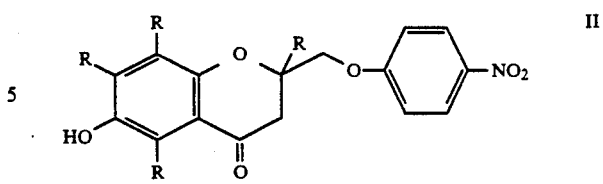

II wherein R has the above-stated meaning, with hydrogen in the presence of a hydrogenation catalyst to give a 6-hydroxy-2,5,7,8-tetraalkyl-2-(4-aminophenoxymethyl)chroman-4-one of the general formula:

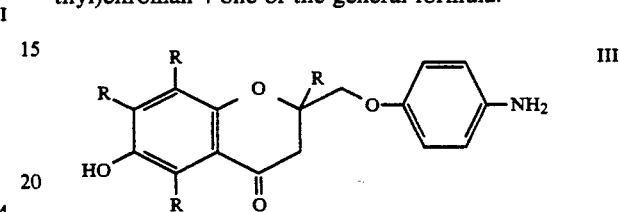

III wherein R has the above stated meaning. In a second step, this aminochromanone is reduced under pressure in the presence of the catalyst system of amorphous zirconium oxide/isopropanol to give a 6-hydroxy-2,5,7,8-tetraalkyl-2-(4-aminophenoxymethyl)chrom-3-ene of the general formula:

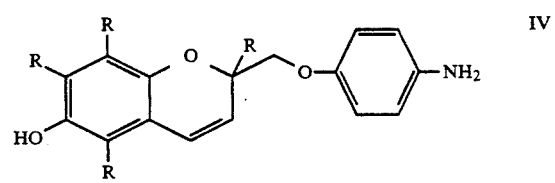

IV where R has the above-stated meaning. In a third step, this aminochromene is finally converted into the final product using hydrogen in the presence of a hydrogenation catalyst.

Preferably the hydrogenation in the first step is carried out with a platinum or palladium catalyst, applied to an inert support. Preferably palladium, applied to carbon in an amount from 0.5 to 10 percent, is employed. Preferably the hydrogenation in the first step is carried out at a hydrogen pressure from 1 to 20 bar and at a temperature between 20° and 100° C. More preferably, the reduction in the second step is carried out at a pressure from 1 to 50 bar and at a temperature of between 80 and 220.C. Preferably the reduction in the second step is carried out at a pressure from 20 to 40 bar and at a temperature of between 160° and 200° C. Preferably, for the reduction, amorphous zirconium oxide is employed which is prepared by precipitation of a zirconyl chloride solution with ammonia and subsequent drying and calcination of the precipitated zirconium oxide. Preferably the amorphous zirconium oxide is subjected to a pretreatment in a mobile inert gas atmosphere at a temperature of between 150° and 300° C. Preferably the hydrogenation catalyst used for the hydrogenation in the third step is a platinum or palladium catalyst, applied to an inert support. Preferably palladium, applied to carbon in an amount from 0.5 to 10 percent, is used. Preferably the hydrogenation in the third step is carried out at a hydrogen pressure from 1 to 20 bar and at a temperature from 15° to 100° C.

These aminochromans of the general formula I are useful intermediates for the preparation of hypolipidaemic pharmaceuticals [J. Med. Chem., 32,, (1989), p. 421]

DETAILED DESCRIPTION OF THE INVENTION

The starting materials are 6-hydroxy-2,5,7,8-tetraalkyl-2-(4-nitrophenoxymethyl)chroman-4-ones (nitrochromanone) of the general formula:

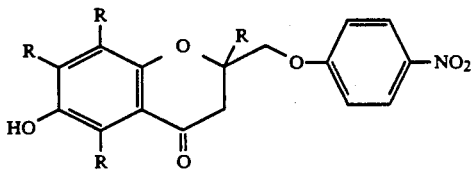

II wherein R has the above-stated meaning. The compounds can be prepared, for example, from acetylhydroquinone derivatives according to European Published Patent Application No. 139,421. Preferably, 6-hydroxy-2,5,7,8-tetramethyl-2-(4-nitrophenoxymethyl)-chroman-4-one (formula II where R is $CH_3$) is used as the starting material.

According to the invention, in the first step, the 6-hydroxy-2,5,7,8-tetraalkyl-2-(4-nitrophenoxymethyl)-chroman-4-one (nitrochromanone) of the general formula II is hydrogenated using hydrogen in the presence of a hydrogenation catalyst to give a 6-hydroxy-2,5,7,8-tetraalkyl-2-(4-aminophenoxymethyl)chroman-4-one (aminochromanone) of the general formula:

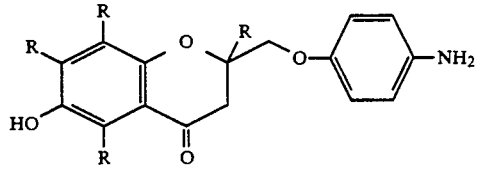

III

The hydrogenation catalysts used are expediently noble metal catalysts, such as, platinum or palladium, applied to an inert support, such as, carbon or alumina. Palladium is preferably used, applied to carbon in an amount from 0.5 to 10 percent.

The hydrogenation is expediently carried out in a lower aliphatic alcohol, such as, ethanol or isopropanol, or, for example, in aromatics, such as toluene, as solvents. Isopropanol has the advantage that a change of solvent ca be omitted for the subsequent step.

The hydrogenation is expediently carried out at a hydrogen pressure of from 1 to 20 bar, preferably 5 to 10 bar, and a temperature of between 20° and 100° C., preferably of between 40° and 60° C. The uptake of hydrogen is as a rule complete after 1 to 2 hours, after which the catalyst can be separated off and the solvent can be evaporated off to isolate the aminochromanone of formula III.

If appropriate, after separation of the catalyst the reaction solution can be employed directly for the subsequent step.

In the second step, according to the invention, the aminochromanone of formula III is reduced under pressure in the presence of the catalyst system of amorphous zirconium oxide/isopropanol to give a 6-hydroxy-2,5,7,8-tetraalkyl-2-(4-aminophenoxymethyl)chrom-3-ene (aminochromene) of the general formula:

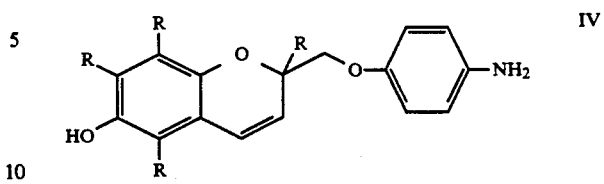

IV

The amorphous zirconium oxide employed according to the invention can be prepared in a known manner by precipitation from a zirconyl chloride solution using sodium hydroxide solution, according to Shibagaki et al., in Bull. Chem. Soc. Japan, 61, (1988), pp. 3283 ff, or using ammonia, according to U.S. Pat. No. 5,030,601, and subsequent drying and calcination. Expediently, the amorphous zirconium oxides prepared have a specific surface area according to BET of between 210 and 265 $m^2/g$. Preferably, an amorphous zirconium oxide is employed which is obtained by precipitation using ammonia.

The amorphous zirconium oxide obtained from the precipitation process is advantageously subjected to a pretreatment before its use. This is expediently carried out by treatment of the precipitated and calcined amorphous zirconium oxide in a mobile inert gas atmosphere at 150° to 300° C. over a period of 1 to 24 hours.

Expediently, the reaction in the second step is carried out by introducing the aminochromanone of formula III together with the pretreated amorphous zirconium oxide in isopropanol, which functions as a reactant and solvent.

The reaction is preferably carried out with exclusion of air at a pressure of between, expediently, 1 to 50 bar, preferably 20 to 40 bar, and a temperature of, expediently, between 80° to 220° C., preferably 160° to 200° C. The reaction is complete after a reaction time of, as a rule, 3 to 10 hours.

The aminochromene of formula IV can be isolated from the reaction mixture after separating off the zirconium oxide catalyst and removing the solvent. However, the reaction solution which contains the aminochromene of the formula IV directly for the subsequent step after separating off the zirconium oxide catalyst can be used.

In the last step, the aminochromene of the formula IV is finally hydrogenated with hydrogen in the presence of a hydrogenation catalyst to give the final product of the formula I. The hydrogenation catalysts used are expediently noble metal catalysts, such as, platinum or palladium, applied to an inert support. Preferably, palladium is employed, applied to carbon in an amount from 0.5 to 10 percent.

The hydrogenation is expediently carried out in a lower aliphatic alcohol, such as, isopropanol, or in aromatics, such as toluene, air in a mixture of toluene and one of the lower aliphatic alcohols.

Expediently, the hydrogenation is carried out at a hydrogen pressure from 1 to 20 bar, preferably 5 to 10 bar, and at a temperature between 15° and 100° C., preferably at 20° to 40° C.

The aminochroman of the formula I can be obtained in a simple manner by removal of the catalyst and removal of the solvent.

EXAMPLES

Preparation of the Amorphous Zirconium Oxide (Procedure A)

Zirconyl chloride octahydrate ($ZrOCl_2.8H_2O$) was dissolved in water. The slight turbidity was filtered off, and the solution was adjusted to a content ($ZrO_2$) of 50 g/l using deionized water. Technical ammonia (about 25 percent) was diluted to a concentration of 10 percent using deionized water. 2.5 liter of deionized water was introduced into a reaction vessel. The zirconyl chloride solution and the ammonia solution were added in a controlled manner while stirring at 8000 rpm. The rate of addition of the $ZrO_2$ solution was 50 ml/min. The ammonia solution was added in such a way that it was possible to maintain a pH of 7.0±0.2 during the resultant precipitation. The solids content of the suspension was kept at about 1 percent by addition of deionized water. After precipitation was complete, the solid was separated off by filtration. The filter cake was washed several times using ammoniacal water until the $Cl^-$ content had been reduced to 0.05 percent. The filter cake was then dried at 100° C., suspended once more, filtered and dried again. Finally, the resultant $ZrO_2$ powder was calcined at 300° C. for 8 hours. The resultant $ZrO_2$ was radiographically amorphous and had a specific surface area according to BET of 240 $m^2$/g.

EXAMPLE 1

(a) Process for the Preparation of 6-hydroxy-2,5,7,8-tetramethyl-2-(4-aminophenoxymethyl)chroman-4-one-(aminochromanone III)

50 g (134.6 mmol) of 6-hydroxy-2,5,7,8-tetramethyl-2-(4-nitrophenoxymethyl)chroman-4-one (II) was introduced into an autoclave together with 2.5 g of a palladium-on-carbon catalyst (5 percent Pd/C) in 150 ml of isopropanol. After flushing several times with nitrogen and then with hydrogen, the mixture was stirred at 750 rpm at a hydrogen pressure of 5 bar and at 50° C. for 1.25 to 1.5 hours. The reaction mixture was then freed from the catalyst. The solvent was evaporated off. 45.7 g (99.5 percent) of the title product were obtained. The purity of the title product was (HPLC) 97 percent.

($b_1$) Process the Preparation of 6-hydroxy-2,5,7,8-tetramethyl-2-4-aminophenoxymethyl)chrom-3-ene (aminochromene IV)

5 g (14.6 the aminochromanone from step 1(a) was introduced into an autoclave with the exclusion of air together with 10 g of amorphous zirconium oxide (prepared according to Procedure A above and pretreated for 2 hours at 200° with the passage of argon) in 100 g of dry isopropanol. After flushing several times with nitrogen, the mixture was heated to a temperature of 190° C. with stirring at 750 rpm and at a pressure of 10 bar. The pressure rose during the course of this heating to 27 to 31 bar. After 8 hours, the reaction mixture was cooled to room temperature and the amorphous zirconium oxide was removed. According to GC, the reaction solution contained the aminochromene (IV) in a yield of 85.3 percent and the aminochroman (I) in a yield of 4.7 percent.

($b_2$) Process for the Preparation of 6-hydroxy-2,5,7,8-tetramethyl-2-(4-aminophenoxymethyl)chrom-3-ene (aminochromene IV)

The reaction was carried out according to Example ($b_1$) but in the presence of 80 g of isopropanol and 20 g of toluene. After removal of the solvent, 4.8 g of product was obtained. Of this product, 87.1 percent is apportioned to the aminochromene (IV) and 3.4 percent to the aminochroman (I).

Process for the Preparation of 6-hydroxy-2,5,7,8-tetramethyl-2-(4-aminophenoxymethyl)chroman (aminochroman I)

The solution containing 85.3 percent of the aminochromene (IV) obtained in Example 1($b_1$) was introduced into an autoclave together with 0.4 g of a palladium-on-carbon catalyst (5 percent Pd/C) and 25 g of toluene. After flushing several times with nitrogen and then with hydrogen, the mixture was stirred at 750 rpm at a hydrogen pressure of 8 bar and at room temperature (24° to 27° C.) for 1.5 hours. The reaction mixture was freed from the catalyst. The solvent was evaporated off. The product (4.6 g) contained the title product in a yield of 81.6 percent.

($c_2$) Process for the Preparation of 6-hydroxy-2,5,7,8-tetramethyl-2-(4-aminophenoxymethyl)chroman (aminochroman I)

The reaction was carried out according to Example 1 ($c_1$) but using 4.8 g of the product from Example 1($b_2$) containing 87.1 percent of the aminochromene IV in the presence of 46.1 of toluene and 5.4 g of methanol as solvents. The crude product (4/6 g) contained the title product in a yield of 92.8 percent (GC).

What is claimed is:

1. A process for the preparation of 6-hydroxy-2,5,7,8-tetraalkyl-2-(4-aminophenoxymethyl)chroman of the formula:

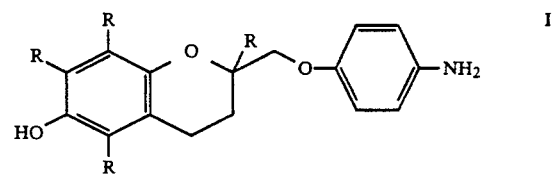

wherein R is a $C_1-C_4$-alkyl group, characterized in that, in a first step, a 6-hydroxy-2,5,7,8-tetraalkyl-2-(4-nitrophenoxymethyl) chroman-4-one of the formula:

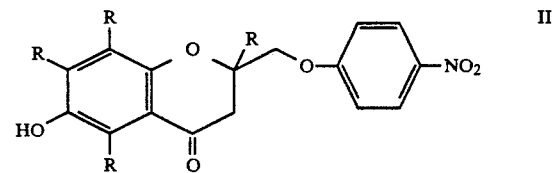

wherein R has the above-stated meaning, is hydrogenated with hydrogen in the presence of a hydrogenation catalyst to give a 6-hydroxy-2,5,7,8-tetraalkyl-2-(4-aminophenoxymethyl)chroman-4-one of the formula:

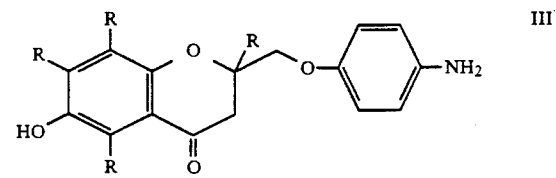

wherein R has the above-stated meaning, in a second step, said aminochromanone of formula III is reduced under pressure in the presence of a catalyst system of amorphous zirconium oxide/isopropanol to give a 6-hydroxy-2,5,7,8-tetraalkyl-2-(4-aminophenoxymethyl)chrom-3-ene of the formula:

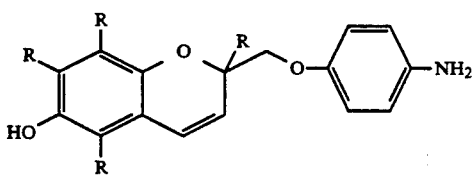

IV wherein R has the above-stated meaning, and in a third step, the aminochromene of formula IV is finally converted into the final product using hydrogen in the presence of a hydrogenation catalyst.

2. The process according to claim 1 wherein the hydrogenation in the first step is carried out with a platinum or palladium catalyst, applied to an inert support.

3. The process according to claim 2 wherein palladium, applied to carbon in an amount from 0.5 to 10 percent, is employed.

4. The process according to claim 3 wherein the hydrogenation in the first step is carried out at a hydrogen pressure from 1 to 20 bar and at a temperature between 20° and 100° C.

5. The process according to claim 4 wherein the reduction in the second step is carried out at a pressure from 1 to 50 bar and at a temperature of between 80° and 220° C.

6. The process according to claim 5 wherein the reduction in the second step is carried out at a pressure from 20 to 40 bar and at a temperature of between 160° and 200° C.

7. The process according to claim 6 wherein, for the reduction, an amorphous zirconium oxide is employed which is prepared by ammoniacal precipitation of a zirconyl chloride solution and subsequent drying and calcination of the precipitated zirconium oxide.

8. The process according to claim 7 wherein the amorphous zirconium oxide is subjected to a pretreatment in a mobile inert gas atmosphere at a temperature of between 150° and 300° C.

9. The process according to claim 8 wherein the hydrogenation catalyst used for the hydrogenation in the third step is a platinum or palladium catalyst, applied to an inert support.

10. The process according to claim 9 wherein the palladium, applied to carbon in an amount from 0.5 to 10 percent, is used.

11. The process according to claim 10 wherein the hydrogenation in the third step is carried out at a hydrogen pressure from 1 to 20 bar and at a temperature from 15° to 100° C.

12. The process according to claim 1 wherein the hydrogenation catalyst used for the hydrogenation in the first and third steps is palladium, applied to carbon in an amount from 0.5 to 10 percent, is employed.

13. The process according to claim 1 wherein the hydrogenation in the first step is carried out at a hydrogen pressure from 1 to 20 bar and at a temperature between 20° and 100° C.

14. The process according to claim 1 wherein the reduction in the second step is carried out at a pressure from 1 to 50 bar and at a temperature of between 80° and 220° C.

15. The process according to claim 14 wherein the reduction in the second step is carried out at a pressure from 20 to 40 bar and at a temperature of between 160° and 200° C.

16. The process according to claim 1 wherein, for the reduction, an amorphous zirconium oxide is employed which is prepared by ammoniacal precipitation of a zirconyl chloride solution and subsequent drying and calcination of the precipitated zirconium oxide.

17. The process according to claim 16 wherein the amorphous zirconium oxide is subjected to a pretreatment in a mobile inert gas atmosphere at a temperature of between 150° and 300° C.

18. The process according to claim 1 wherein the hydrogenation catalyst used for the hydrogenation in the third step is a platinum or palladium catalyst, applied to an inert support.

19. The process according to claim 18 wherein the palladium, applied to carbon in an amount from 0.5 to 10 percent, is used.

20. The process according to claim 1 wherein the hydrogenation in the third step is carried out at a hydrogen pressure from 1 to 20 bar and at a temperature from 15° to 100° C.

* * * * *